(12) United States Patent
Vervest

(10) Patent No.: US 9,006,422 B2
(45) Date of Patent: Apr. 14, 2015

(54) OXIDATION PROCESS FOR PREPARING 3-FORMYL-CEPHEM DERIVATIVES

(75) Inventor: Ivan Joseph Maria Vervest, Beerse (BE)

(73) Assignee: Basilea Pharmaceutica International Ltd., Basel (CH)

( * ) Notice: Subject to any disclaimer, the term of this patent is extended or adjusted under 35 U.S.C. 154(b) by 0 days.

(21) Appl. No.: 13/696,151

(22) PCT Filed: May 9, 2011

(86) PCT No.: PCT/EP2011/057404
§ 371 (c)(1),
(2), (4) Date: Nov. 26, 2012

(87) PCT Pub. No.: WO2011/141415
PCT Pub. Date: Nov. 17, 2011

(65) Prior Publication Data
US 2013/0066065 A1 Mar. 14, 2013

(30) Foreign Application Priority Data
May 10, 2010 (EP) ..................................... 10162407

(51) Int. Cl.
*C07D 501/34* (2006.01)
(52) U.S. Cl.
CPC ..................................... *C07D 501/34* (2013.01)
(58) Field of Classification Search
CPC ...................................................... C07D 501/34
USPC ................................................. 540/217, 228
See application file for complete search history.

(56) References Cited

U.S. PATENT DOCUMENTS 6,504,025 B2 * 1/2003 Hebeisen et al. ............. 540/222

OTHER PUBLICATIONS

De Mico. J. Org. Chem. 62 (2007), 6974-6977.*
Greene. Protective Groups in Organic Synthesis. n.p.: Wiley, 1999. eBook Collection (EBSCOhost).*
Anelli, Pier. J. Org. Chem., vol. 52, No. 12, 1987.*

* cited by examiner

*Primary Examiner* — Golam M M Shameem
*Assistant Examiner* — Laura Daniel

(57) ABSTRACT

The present invention relates to an improved process for oxidizing 3-hydroxy-methyl-cephem derivatives to the corresponding 3-formyl-cephem derivatives. In particular this oxidation process is for the preparation of 7-[2-(5-amino-[1,2,4]thia-diazol-3-yl)-2-hydroxyimino-acetylamino]-3-formyl-8-oxo-5-thia-1-aza-bicyclo[4.2.0]oct-2-ene-2-carboxylic acid derivatives of formula (I) using a combination of a hypervalent iodine oxidizing agent of the type 10-I-3 such as bis(acetoxy)iodo-benzene (BAIB) and a catalyst such as 2,2,6,6-tetramethyl-1-piperidinyloxy (TEMPO). These compounds of formula (I) are intermediates in the synthesis of ceftobiprole.

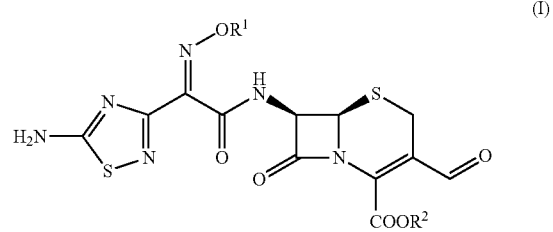

(I)

9 Claims, No Drawings

OXIDATION PROCESS FOR PREPARING 3-FORMYL-CEPHEM DERIVATIVES

This application is a National Stage Application of PCT/EP2011/057404 filed May 9, 2011, which claims priority from European Patent Application 10162407.0 filed on May 10, 2010. The priority of both said PCT and European Patent Application are claimed.

BACKGROUND OF THE INVENTION

The present invention relates to an improved process for oxidizing 3-hydroxy-methyl-cephem derivatives to the corresponding 3-formyl-cephem derivatives. In particular this oxidation process is for the preparation of 7-[2-(5-amino-[1,2,4]thia-diazol-3-yl)-2-hydroxyimino-acetylamino]-3-formyl-8-oxo-5-thia-1-aza-bicyclo[4.2.0]oct-2-ene-2-carboxylic acid derivatives of formula (I) using a combination of a hypervalent iodine oxidizing agent of the type 10-I-3 such as bis(acetoxy)iodo-benzene (BAIB) and a catalyst such as 2,2,6,6-tetramethyl-1-piperidinyloxy (TEMPO). These compounds of formula (I) are intermediates in the synthesis of ceftobiprole.

Ceftobiprole is a parenterally administered cephalosporin with high affinity for most penicillin-binding proteins, including the mecA product penicillin binding protein (PBP) 2a, rendering it active against methicillin-resistant *Staphylococcus aureus* (MRSA). Ceftobiprole shows broad-spectrum activity against relevant resistant Gram-positive and Gram-negative pathogens in vitro and has a low liability to induce resistance. It is administered in vivo as a water soluble prodrug, ceftobiprole medocaril, which is rapidly cleaved in plasma to form ceftobiprole, diacetyl and $CO_2$. The chemical structure of ceftobiprole and ceftobiprole medocaril are shown below.

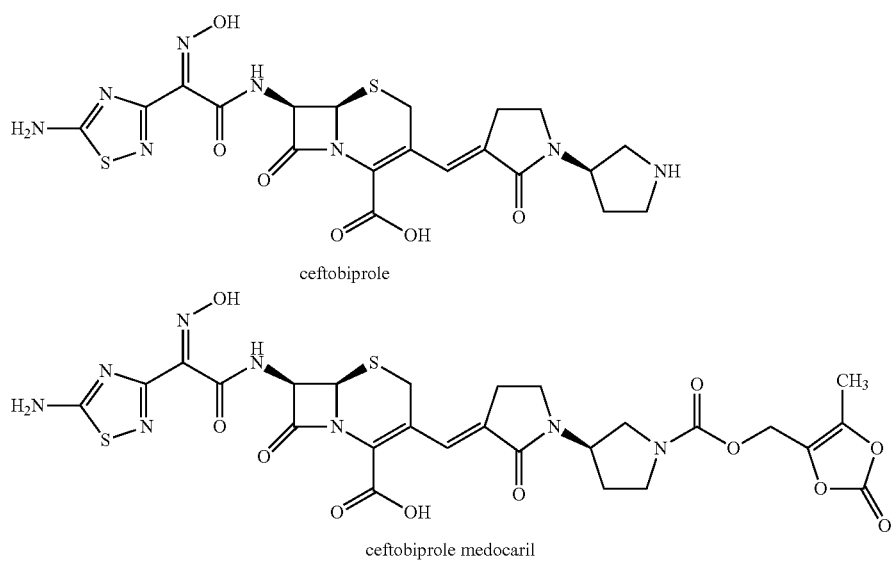

ceftobiprole ceftobiprole medocaril

Compounds of formula (I) and methods for preparing these compounds have been disclosed in WO-01/90111. WO-01/90111 also discloses a process for the preparation of ceftobiprole. Other methods for the preparation of ceftobiprole are disclosed in WO-99/65920 and Drugs of the Future, 30(1), p. 11-22 (2005).

WO-01/90111 discloses two oxidation procedures (Example 2 on page 16) for oxidizing 3-hydroxy-methyl-cephem derivatives of formula (II) to the corresponding 3-formyl-cephem derivatives of formula (I):

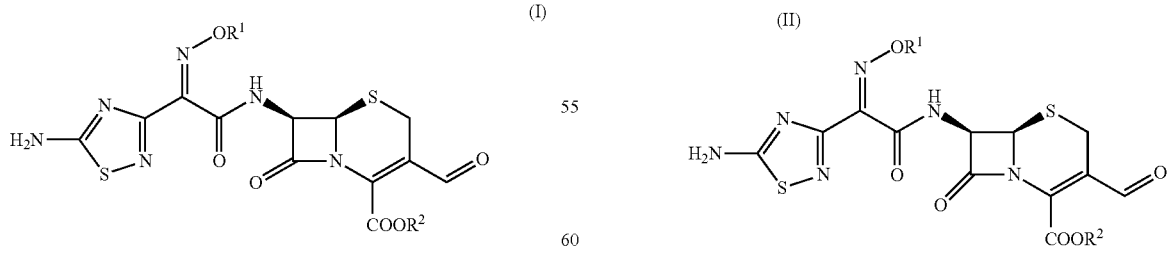

The first oxidation procedure disclosed in WO-01/90111 uses a mixture of an inorganic hypohalite such as sodium hypochlorite and 2,2,6,6-tetramethyl-1-piperidinyloxy (TEMPO) whereby the reaction mixture is a two-phase mixture of water and dichloromethane that is vigorously stirred. Substituent $R^1$ is a hydroxy protecting group (triphenylmethyl group) and $R^2$ is a carboxylic acid protecting group, (diphenylmethyl). The reported yield is 74%.

The second oxidation procedure disclosed in WO-01/90111 uses $MnO_2$ as the oxidizing agent suspended in a mixture of tetrahydrofuran and dichloromethane. The reported yield is 52%.

In general the present invention concerns the oxidation of a primary alcohol to an aldehyde using an oxidizing agent. A number of art known oxidizing agents are known such as Jones reagent (chromic acid and sulfuric acid in water), Collins reagent (dipyridine Cr(VI) oxide), Dess-Martin periodinane, pyridinium chlorochromate (PCC), pyridinium dichromate (PDC), $MnO_2$, o-iodoxy benzoic acid (IBX), methyl-2-iodoxy benzoate, isopropyl-2-iodoxy benzoate, trichloro isocyanuric acid, and a combination of TEMPO with an inorganic hypochlorite. The selection of the most suitable oxidizing agent is a cumbersome process wherein issues such as over-oxidation to a carboxylic acid, yield, impurities, cost, reaction time, scale-up possibilities, and the like have to be evaluated in order to achieve the best results.

The oxidation procedures to convert 3-hydroxymethyl-cephem derivatives of formula (II) to the corresponding 3-formyl-cephem derivatives of formula (I) as disclosed in WO-01/90111 (Example 2 on page 16) have the following disadvantages:
  low yield: 52% when $MnO_2$ is used
  low yield: 74% when a combination of sodium hypochlorite and TEMPO as oxidizing agent is used
  sodium hypochlorite needs to be carefully dosed in a continuous way to minimise over-oxidation (formation of S-oxides)
  heterogeneous two-phase system of water and dichloromethane that needs to be stirred vigorously
  large volume of solvent is needed: about 7.6 litre/mol.

SUMMARY OF THE INVENTION

It has now been found that the above mentioned disadvantages for the oxidation of 3-hydroxymethyl-cephem derivatives of formula (II) to the corresponding 3-formyl-cephem derivatives of formula (I) can be overcome when using a combination of a hypervalent iodine oxidizing agent of the type 10-I-3 such as bis(acetoxy)iodobenzene (BAIB) and a catalyst as 2,2,6,6-tetramethyl-1-piperidinyloxy (TEMPO). This oxidation system uses a catalytic amount of TEMPO ranging from 0.05 mol to 0.2 mol and a slight excess of BAIB in an amount from 1 mol to 1.2 mol. BAIB regenerates the TEMPO that is being consumed during the oxidation reaction in order to close the catalytic cycle. This oxidation procedure has the following advantages:
  improved yield : up to 84%
  improved purity ranging from 92.8 to 97.9% (purity measured using LC), compared to a purity of 83 to 92% when the above mentioned procedure from the prior art was reproduced in-house
  no issues with addition rate of the oxidizing agent and no over-oxidation, thereby resulting in higher product quality
  one organic phase and therefore no need for vigorous stirring, therefore easier and more robust to scale-up
  lower volume of solvent used: 2 to 5 litre/mol.

DETAILED DESCRIPTION OF THE INVENTION

The present invention concerns a process for the preparation of a 7-[2-(5-amino-[1,2,4]thiadiazol-3-yl)-2-hydroxyimino-acetylamino]-3-formyl-8-oxo-5-thia-1-aza-bicyclo[4.2.0]oct-2-ene-2-carboxylic acid derivative of formula (I)

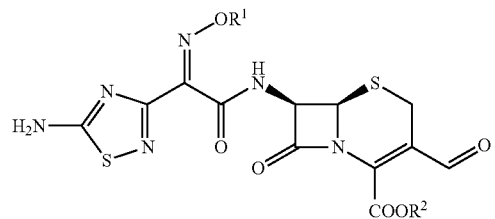

wherein $R^1$ is a hydroxy protecting group and $R^2$ is a carboxylic acid protecting group, which process is characterized in that it comprises oxidizing a compound of formula (II)

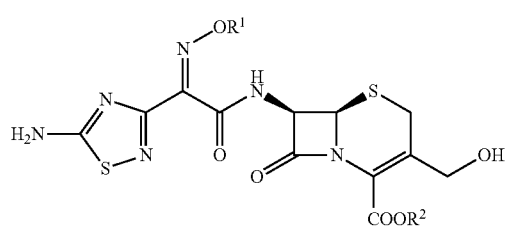

with a combination of a hypervalent iodine oxidizing agent of the type 10-I-3 such as bis(acetoxy)iodo-benzene (BAIB) or [bis(1,1,1-trifluoroacetoxy)iodo]benzene (BTIB) and a catalyst selected from 2,2,6,6-tetramethyl-1-piperidinyloxy (TEMPO), 4-hydroxy-2,2,6,6-tetramethyl-1-piperidinyloxy and 4-(acetylamino)- 2,2,6,6-tetramethyl-1-piperidinyloxy in a suitable solvent.

The term "hydroxy protecting group" as used herein defines a protecting group which is generally used to replace a hydrogen of the hydroxyl group. Examples of such a group is e.g. benzyl, phenylethyl, naphthalenylmethyl, triphenylmethyl, or a tri($C_{1-6}$alkyl)silyl such as e.g. trimethylsilyl, or tert-butyl-dimethylsilyl. A commonly used hydroxy protecting group is a triphenylmethyl group (also called a trityl group).

The term "carboxylic acid protecting group" as used herein defines a protecting group which is generally used to replace a hydrogen of the carboxyl group. Examples of such a group is e.g. diphenylmethyl, tert-butyl, p-nitrobenzyl, p-methoxybenzyl, methoxymethyl and the like. Diphenylmethyl is a commonly used carboxylic acid protecting group.

The term "$C_{1-6}$alkyl" as used herein defines straight and branched chain saturated hydrocarbon radicals having from 1 to 6 carbon atoms such as, for example, methyl, ethyl, propyl, butyl, 1-methylethyl, 2-methylpropyl, 2-methylbutyl, pentyl, hexyl and the like.

Hypervalent iodine oxidizing agent of the type 10-I-3 have been described by De Mico A. et al. in J. Org. Chem., 62, 6974-6977 (1997) such as bis(acetoxy)iodo-benzene (BAIB) or [bis(1,1,1-trifluoroacetoxy)iodo]benzene (BTIB).

The amount of catalyst selected from 2,2,6,6-tetramethyl-1-piperidinyloxy (TEMPO), 4-hydroxy-2,2,6,6-tetramethyl-1-piperidinyloxy and 4-(acetylamino)-2,2,6,6-tetramethyl-1-piperidinyloxy ranges between 0.05 and 0.2 mol with respect to the compound of formula (II) and the amount of hypervalent iodine oxidizing agent of the type 10-I-3 ranges between 1 mol and 1.2 mol with respect to the compound of formula (II). In practice the amount of catalyst is usually 0.1 mol and the amount of hypervalent iodine oxidizing agent of the type 10-I-3 is 1.1 mol with respect to the compound of formula (II).

Suitable solvents for use in the oxidation process of the present invention are selected from halogenated hydrocarbons such as dichloromethane; esters such as ethyl acetate; ethers such as tetrahydrofuran; hydrocarbons such as toluene; polar solvents such as acetone and acetonitrile; and solvent mixtures thereof, such as solvent mixtures of dichloromethane with tetrahydrofuran, acetonitrile, or ethylacetate, solvent mixtures of ethyl acetate with tetrahydrofuran, and solvent mixtures of toluene with tetrahydrofuran.

EXAMPLES

Experimental Part
General Oxidation Procedure 1 mol of 7-[2-(5-amino-[1,2,4]thiadiazol-3-yl)-2-trityloxyimino-acetylamino]-3-hydroxymethyl-8-oxo-5-thia-1-aza-bicyclo[4.2.0]oct-2-ene-2-carboxylic acid benzhydryl ester (compound 2) was added to a reaction vessel solvent was added and cooled to 10° C.

0.10 mol of catalyst selected from 2,2,6,6-tetramethyl-1-piperidinyloxy (TEMPO), 4-hydroxy-2,2,6,6-tetramethyl-1-piperidinyloxy and 4-(acetylamino)- 2,2,6,6-tetramethyl-1-piperidinyloxy was added stirred for another 5 minutes 1.1 mol of a hypervalent iodine oxidizing agent of the type 10-I-3 selected from bis(acetoxy)iodo-benzene (BAIB) was added stirred till complete conversion (as measured by LC)

work-up procedure:

the reaction product was precipitated by the addition of an anti-solvent such as cyclohexane (other suitable anti-solvents are methylcyclohexane, isooctane, diisopropylether and cyclopentylmethylether)

precipitate was filtered off precipitate was washed isolated 7-[2-(5-amino-[1,2,4]thiadiazol-3-yl)-2-trityloxyimino-acetylamino]-3-formyl-8-oxo-5-thia-1-aza-bicyclo[4.2.0]oct-2-ene-2-carboxylic acid benzhydryl ester (compound (1)) was dried at 30° C. under vacuum Results: catalyst is TEMPO (2,2,6,6-tetramethyl-1-piperidinyloxy) and hypervalent iodine oxidizing agent of the type 10-I-3 is BAIB

| solvent | TEMPO # eq. | BAIB # eq | purity of compound 1 | isolated yield mol % |
|---|---|---|---|---|
| $CH_2Cl_2$ (10 L/mol) | 0.1 mol | 1.1 mol | 95.6% | 81.1 |
| $CH_2Cl_2$ (5 L/mol) | 0.1 mol | 1.1 mol | 96.1% | 81.9 |
| ethylacetate (5 L/mol) | 0.1 mol | 1.1 mol | 95.3% | 58.2 |
| THF (2 L/mol) | 0.1 mol | 1.1 mol | 96.3% | 72.7 |
| acetonitril (3 L/mol) | 0.1 mol | 1.1 mol | 97.9% | 64.2 |
| $CH_2Cl_2$/THF (2 L/mol/1 L/mol) | 0.1 mol | 1.1 mol | 93.2% | 83.9 |
| $CH_2Cl_2$/acetonitril (2.5 L/mol/0.5 L/mol) | 0.05 mol | 1.1 mol | 95.6% | 81.7 |
| $CH_2Cl_2$/acetonitril (2.25 L/mol/0.75 L/mol) | 0.05 mol | 1.05 mol | 92.8% | 78.1 |

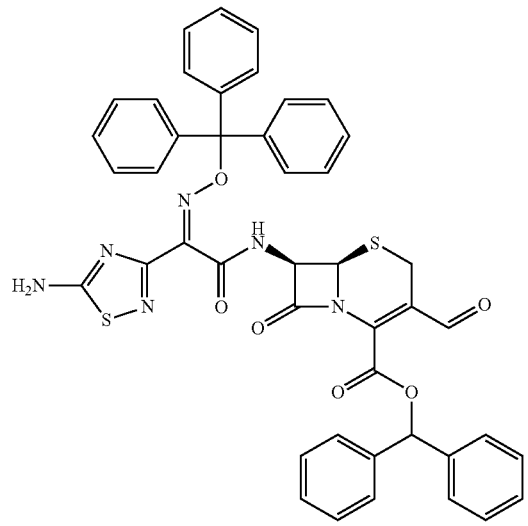

7-[2-(5-amino-[1,2,4]thiadiazol-3-yl)-2-trityloxyimino-acetylamino]-3-formyl-8-oxo-5-thia-1-aza-bicyclo[4.2.0]oct-2-ene-2-carboxylic acid benzhydryl ester Compound (2)

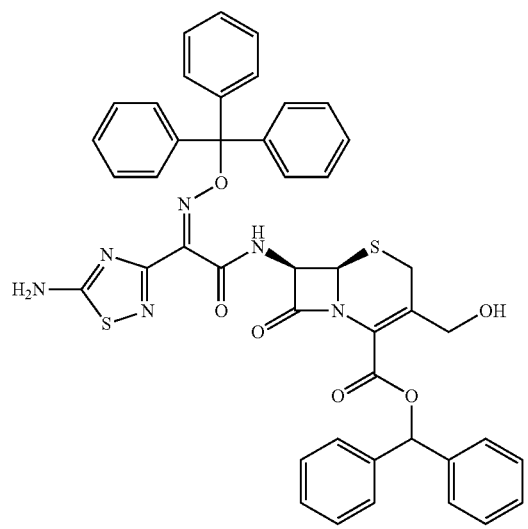

7-[2-(5-amino-[1,2,4]thiadiazol-3-yl)-2-trityloxyimino-acetylamino]-3-hydroxymethyl-8-oxo-5-thia-1-aza-bicyclo[4.2.0]oct-2-ene-2-carboxylic acid benzhydryl ester

The invention claimed is:
1. A process for the preparation of 7-[2-(5-amino-[1,2,4]thiadiazol-3-yl)-2-hydroxy-imino-acetylamino]-3-formyl-8-oxo-5-thia-1-aza-bicyclo[4.2.0]oct-2-ene-2-carboxylic acid derivative of formula (I)

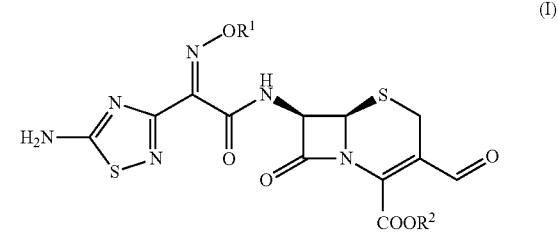

wherein $R^1$ is a hydroxyl protecting group and $R^2$ is a carboxylic acid protecting group, which process is characterized in that it comprises oxidizing a compound of formula (II)

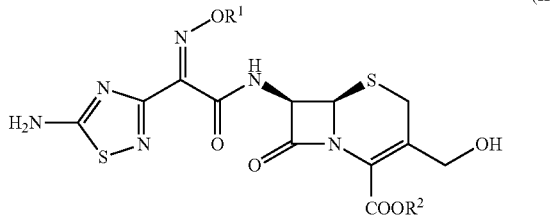

(II)

with a combination of a hypervalent iodine oxidizing agent of the type 10-I-3 and a catalyst selected from 2,2,6,6-tetramethyl-1-piperidinyloxy (TEMPO), 4-hydroxy-2,2, 6,6-tetramethyl-1-piperidinyloxy and 4-(acetylamino)- 2,2,6,6-tetramethyl-1-piperidinyloxy in a solvent selected from the group consisting of dichloromethane, mixtures of dichloromethane and tetrahydrofurane and mixtures of dichloromethane and acetonitrile.

2. The process as claimed in claim 1 wherein the hypervalent iodine oxidizing agent is selected from bis(acetoxy)iodobenzene (BAIB) or [bis(1,1,1-trifluoroacetoxy) -iodo]benzene (BTIB).

3. The process as claimed in claim 2 wherein the hypervalent iodine oxidizing agent is bis(acetoxy)iodobenzene (BAIB).

4. The process as claimed in claim 3 wherein the hydroxyl protecting group $R^1$ is selected from benzyl, phenylethyl, naphthalenylmethyl,triphenylmethyl, or a tri($C_{1-6}$alkyl)silyl, and the carboxylic acid protecting group $R^2$ is selected from diphenylmethyl, tert-butyl, p-nitrobenzyl, p-methoxybenzyl, methoxymethyl.

5. The process as claimed in claim 4 wherein $R^1$ is triphenylmethyl and $R^2$ is selected from diphenylmethyl.

6. The process as claimed in claim 5 wherein the catalyst is 2,2,6,6-tetramethyl -1-piperidinyloxy (TEMPO).

7. The process as claimed in claim 5 wherein the amount of catalyst ranges between 0.05 and 0.2 mol with respect to the compound of formula (II) and the amount of BAIB ranges between 1 mol and 1.2 mol with respect to the compound of formula (II).

8. The process as claimed in claim 7 wherein the amount of catalyst is 0.1 mol and the amount of BAIB is 1.1 mol with respect to the compound of formula (II).

9. The process as claimed in claim 6 wherein the amount of catalyst ranges between 0.05 and 0.2 mol with respect to the compound of formula (II) and the amount of BAIB ranges between 1 mol and 1.2 mol with respect to the compound of formula (II).

* * * * *